United States Patent
Kuznetsov

Patent Number: 5,783,449
Date of Patent: Jul. 21, 1998

[54] METHOD FOR QUANTIFYING ALCOHOL CATABOLISM

[76] Inventor: Oleg Kuznetsov, 322 Veazie St., #B, Providence, R.I. 02904

[21] Appl. No.: 736,671

[22] Filed: Oct. 25, 1996

[51] Int. Cl.$^6$ .................................................. G01N 33/497
[52] U.S. Cl. .......................................... 436/132; 436/900
[58] Field of Search .................................. 436/132, 900; 422/89

[56] References Cited

PUBLICATIONS

Biosis 96:196365, 1996.
Fujimiya et al., "Problems in pharmacokinetic analysis of alcohol disposition: A trial of the Bayesian least–squares method", Alcoholism Clinical and Experimental Research 20(1 suppl.). 1996, 2A–6A, ISSN:0145–6008. Biosis 96:196365 abstract.

Primary Examiner—Lyle A. Alexander

[57] ABSTRACT

The method for quantifying Alcohol Breakdown Activity (ABA) in humans in vivo is developed to determine an efficiency of alcohol catabolism for any given individual. Unlike other related methods, Index-K uses a biological regularity of ABA and employs a third dimension for integrating the multiple pharmacokinetical data into a single value. As expected, it allows for the discrimination between human differences, including gender and personal levels of alcohol dependency. Its use of pharmacokinetical data from ethanol catabolism makes it absolutely specific to alcohol—a major cause of alcohol disorder. This feature allows us to help diagnose alcoholism even in cases where traditional methods used to evaluate harmful alcohol consumption have failed.

2 Claims, 3 Drawing Sheets

METHOD FOR QUANTIFYING ALCOHOL CATABOLISM

BACKGROUND OF THE INVENTION

Measuring the amount of an alcohol (ethanol) in humans is routinely done for a variety of scientific, legal and medical reasons. One of the most important reasons is to determine the effective biological marker to alcoholism, which affects more than 10 percent of the American adult population. A common method of measurement is the Blood (or Breath) Alcohol Concentration (BAC). However, no single dependent variable has been proposed as a result of such measurements, which can be used as a pharmacokinetic biological marker of alcoholism. Moreover, the studies performed in the past 50 years have been inconclusive on such factors as ethnic background, gender, or participants' stage of alcohol dependency. One reason for this failure is that existing pharmacokinetic data evaluation methods use a two-dimensional approach which takes into account only the concentration of the alcohol versus time. A second reason is a different approach taken to the mode of alcohol intake.

The present invention benefits from the standardized alcohol intake, while expanding on the BAC approach by utilizing a multidimensional way of managing pharmacokinetical data. This is done by considering specific enzymatic body actions multiplied by other mechanisms of alcohol elimination to determine individual differences in Alcohol Breakdown Activity (ABA). The internal regularity of the ABA nature is then employed in an instrument termed the Index-K to provide eventually new diagnostic tool for alcoholism as set forth in this specification.

DESCRIPTION OF THE PRIOR ART

Testing devices relating to alcohol consumption are well known. Many are based on readings taken from the subject's breath. For example, in U.S. Pat. No. 3,823,601 to Hoppesch, catalytic and semiconductor detector elements respond differently to alcoholic and non-alcoholic breath. A predetermined breath alcohol concentration could be indicated by an electronic response. In U.S. Pat. No. 4,770,026 to Wolf, breath alcoholic content is determined by measuring flow of electrons obtained from oxidation of breath alcohol on the surface of the fuel cell. An infrared sensing device is used for determining the concentration of alcohol in deep lung breath and alveoli from the breath sample in U.S. Pat. No. 5,376,555 to Forrester et al. And in U.S. Pat. No. 5,443,794 to Williams, a volatile component concentration in the gas, such as breath with alcohol contamination, is measured. The apparatus is particularly suited for breath testing, to see that breath alcohol concentration does not exceed legal limits. The present invention seeks to quantify alcohol catabolic activity in humans using the readings from repeat measurements of body alcohol concentration and employing a new method for managing pharmacokinetical data especially designed for this purpose as set forth herein.

SUMMARY OF THE INVENTION

An innovative Index-K is used to help in diagnosing an alcohol disorder in humans by taking into account individual differences in Alcohol Breakdown Activity (ABA).

Using the Index-K instrument, a variety of pharmacokinetical data is integrated into a single value which is defined as the ratio between descending Area Under a plotted Curve (AUC) and the ascending AUC for a pharmacokinetical curve. This ratio presents the individual's quantitative assessment of the efficiency of ABA over displaying commensurability of the alcohol elimination power by virtue of the protection barriers for alcohol absorption. When the values of the of Index-K of 5.89 or higher, compare to non-alcoholic male subjects having a value of 2.74, there is a quite reasonable, positive association with alcohol disorder.

It is the primary objective of the present invention to provide the method for quantitatively determining a person's efficiency of alcohol catabolization.

Another objective is to provide a new diagnostic tool for alcoholism—finally, entirely specific to ethanol.

Yet another objective is to determine an individual's biological verge between relatively "safe" and pathological consumption of alcohol.

A final objective is to emphasize the different way female humans process alcohol from non-alcoholic males.

These objectives and advantages of the present invention will become apparent to readers after considering the ensuing description and accompanying drawings.

DESCRIPTION OF THE PREFERRED EMBODIMENT

Today the evaluation of harmful alcohol consumption is based on an unclear quantitative definition of hazardous drinking which is corroborated by the elevation of the levels in liver blood tests with positive scores on the CAGE (Cut down drinking, Annoyed, felt Guilty, needed Eye-opener) and Short Michigan Alcoholism Screening Test (SMAST) questionnaires. This assessment is quite imprecise because similar doses of alcohol affect people differently. At the same time the blood markers (e.g., SGOT, or Aspartate aminotransferase; τGGT or τ-Glutamyltransferase; SGPT or Alanine aminotransferase, etc.) are not specific for alcohol. Also, the questionnaires identification is rather subjective.

Measured and counted pharmacokinetic changes have produced no single dependent variable which can be used as a biological marker of alcoholism. This is due to the fact that existing methods of evaluation of pharmacokinetical data are strictly two-dimensional; namely, the concentration of alcohol versus time. Such two-dimensional quantification of alcohol pharmacokinetic data makes subgroup differentiation extremely difficult and precludes even a comparison (e.g., BAC versus Transdermal Alcohol Level—TAL) applied to a single individual during the same experimental session. The present invention seeks to use an innovative pharmacokinetical Index-K which utilizes an additional criterion accounting for individual differences in Alcohol Break Down Activity (ABA).

It is well known that catabolism of alcohol in the human body depends primarily upon specific enzymatic activity, mainly Alcohol Dehydrogenase (ADH), which begins converting ethanol in liver to such final products as carbon dioxide and water. In addition, approximately one-fifth of consumed alcohol is destroyed by the Microsomal Ethanol-Oxidation System (MEOS). Also, it is well known that chronic drinking will make for a less efficient MEOS mechanism to destroy the alcohol consumed. Other factors, such as some sexual hormones which influence another extrahepatic way of alcohol catabolism by mucosal gastric ADH activity, are also known. These factors, and other still-unknown mechanisms, are activated during ABA and proceed through at least three pharmacokinetical phases: i.e., absorption, distribution and elimination. That is why with ethanol, a strongly hydrophilic substance with a relatively low molecular weight, the distribution occurs almost immediately within the absorption phase.

Figure 1:
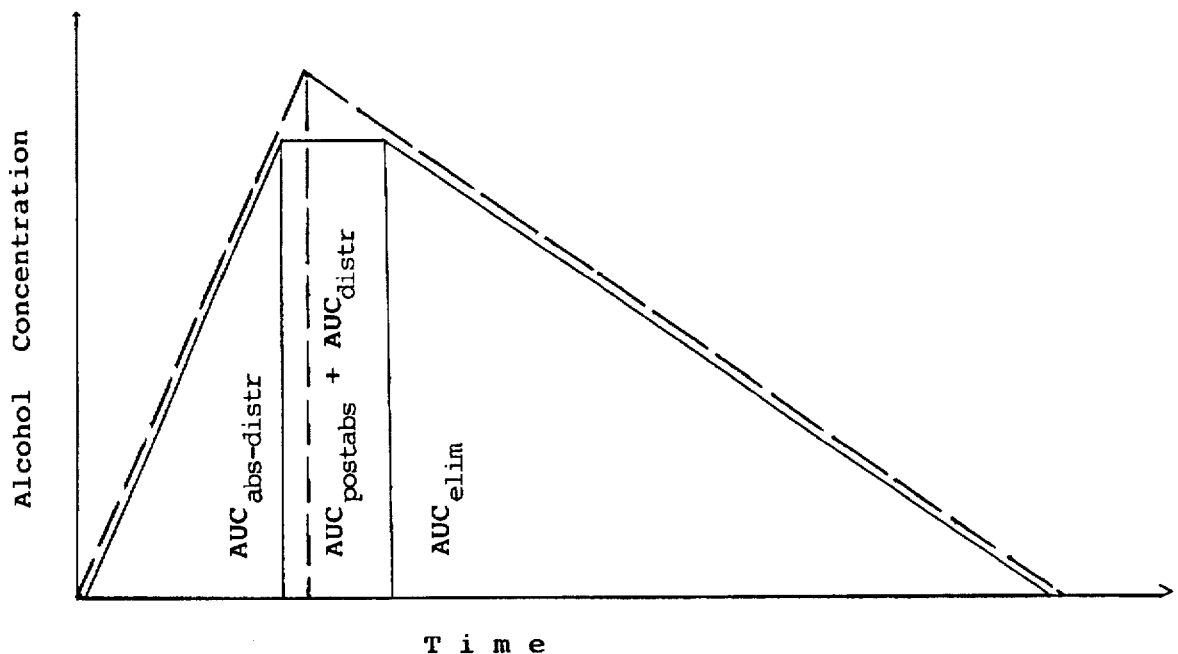
FIG. 1 is an oversimplified graphic representation of the factors used in the Index-K formula.

Because alcohol has a comparatively low chemical reactivity, a biochemical neutralizing process (elimination phase) needs more time and energy than absorption and distribution phases. Consequently, as shown in FIG. 1, the Area Under the Curve (AUC) for the elimination phase (the right, greater subtriangle obtained by dividing the main triangle with a bisecting line) is always larger than the AUC for the others two phases (the left, lesser subtriangle). Even though ethanol elimination begins at very outset of consumption, formally the process breaks out from an apex into a pharmacokinetical curve—the break point of a neutralizing reaction against extreme absorption-distribution action. This specific physiological-pharmacokinetic feature has been used to implement the present invention because the Index-K is defined as the ratio of AUC elimination to AUC absorption-distribution. The FIG. 1 curves show oversimplified graphic representation for two possible ways (triangle or trapezium) of alcohol catabolism in humans over time, where:

$AUC_{abs-distr}$ is the absorption-distribution of ethanol and is equal to the AUC under the ascending part of the curve;

$AUC_{postabs}+AUC_{distr}$ is a sum of the postabsorption and distribution of ethanol and is equal to the AUC between the ascending and descending part of the plotted curve. Because most pharmacokinetical cases have a triangle-like shape for the curve, it obviously has no value. However, if the value occurs (in a case with a trapezium-like shape for the curve) it disregards from calculation, because proportional representation for this internal rectangular-like composite AUC is the same as the Index-K value;

and $AUC_{elim}$ is the elimination of ethanol and is equal to the AUC under the descending part of the pharmacokinetical curve.

To verify the results, after ethanol consumption, BAC levels were repeatedly measured by INTOXIMETER EC/IR 3000, until two successive zero BAC measurements were obtained. Because the consumed alcohol was eliminated through the skin as well as through the lungs, mucous membranes and kidneys, the Transdermal Alcohol Level (TAL) was simultaneously measured in some cases with BAC by a wearable device, the Transdermal Alcohol Sensor/Recorder (TAS). A special electrochemical membrane measured oxidation by transdermal ethanol. The resulting current measured is expressed in micro Amperes ($\mu A$) and was automatically multiplied by 35 for TAS#37; by 40 for TAS#34, TAS#39, or by 45 for TAS#33 depending on type of construction for the device.

Figure 2:
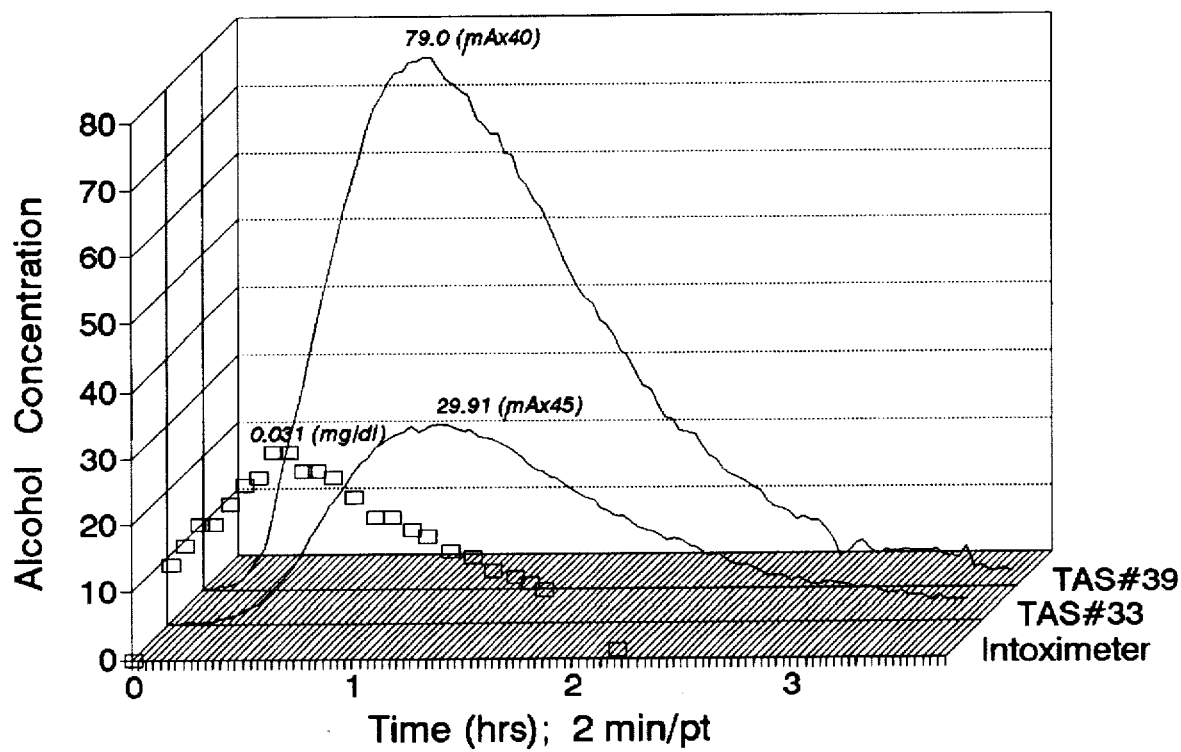
FIG. 2 compares the values of the Index-K using three separate sources of the pharmacokinetical data simultaneously obtained from the same individual.

The present invention allows us to characterize the internal body regularity of Alcohol Breakdown Activity (ABA) even when taken into consideration the numerous pharmacokinetic measurements obtained using different methods on the same individual. As the data from FIG. 2 indicate, values obtained for Index-K remained relatively constant (1.9÷1.97), despite a 2.7-fold variation in the amplitude of the other curves. It also equalized the 1.9-fold variation of the "elimination time" and the 1.7-fold variation of the "time to peak" differences, which happen to be a deadly snare for two-dimensional evaluation methods. This suggests conformity with an internal law for the catabolism of alcohol in a given subject. The following table of results describes the FIG. 2 curves:

TABLE 1

| METHOD: | Breath Alcohol Concentration | Transdermal Alcohol Levels (different body location) | |
|---|---|---|---|
| EQUIPMENT: DATA: | Intoximeter 3000 | TAS#33 | TAS#39 |
| Elimination time | 132' | ≧218' | ≧220' |
| Time to peak | 40' | 74' | 60' |
| Peak value | 31 (mg/dl) | 29.91 ($\mu Ax45$) | 79.0 ($\mu Ax40$) |
| Peak delay time | — | 34' | 20' |
| Elimination delay | — | ≧86' | ≧88' |
| AUC before peak | 692 | 993.54 | 2301.63 |
| AUC after peak | 1346.997 | 1890.076 | 4543.425 |
| Integrated AUC | 2162.997 | 2883.615 | 6845.058 |
| Index-K | 1.95 | 1.9 | 1.97 |

Figure 3:
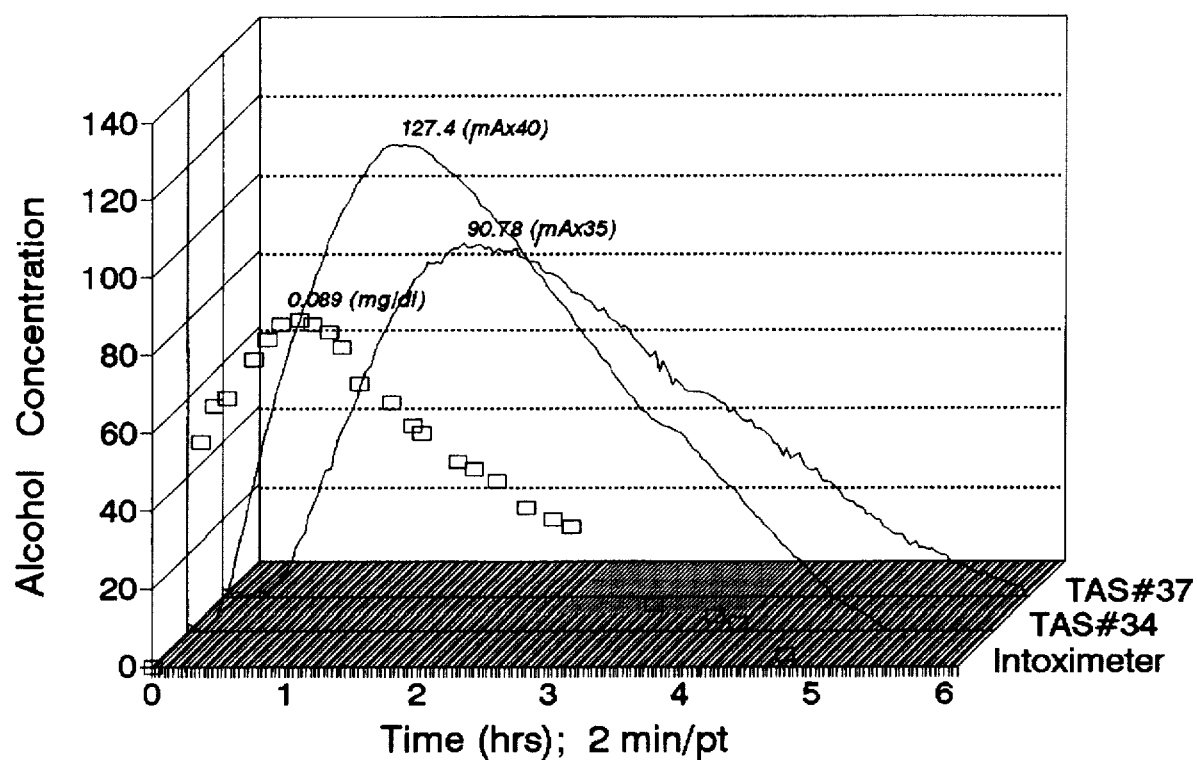
FIG. 3 is an extension of illustration for FIG. 2.

A similar example for the standardized alcohol intake is presented in FIG. 3 where curves yielded the following tabular results:

TABLE 2

| METHOD: | Breath Alcohol Concentration | Transdermal Alcohol Levels (different body location) | |
|---|---|---|---|
| EQUIPMENT: DATA: | Intoximeter 3000 | TAS#34 | TAS#37 |
| Elimination time | 294' | 326' | 374' |
| Time to peak | 66' | 92' | 108' |
| Peak value | 89 (mg/dl) | 127.4 ($\mu Ax40$) | 90.78 ($\mu Ax35$) |
| Peak delay time | — | 26' | 42' |
| Elimination delay | — | 34' | 80' |
| AUC before peak | 4011 | 6261.78 | 4636.25 |
| AUC after peak | 9118.053 | 14674.71 | 11680.25 |
| Integrated AUC | 13129.05 | 20936.48 | 16316.45 |
| Index-K | 2.27 | 2.34 | 2.5 |

BAC tests were conducted on 83 volunteer individuals, 48 of whom were non-alcoholic males, 27 of whom were non-alcoholic females and 8 of whom were alcoholic males. A standardized alcohol intake was administered and an analysis of obtained data indicated about twice the highest ratio of the value of Index-K between alcoholic 5.89 (standard deviation-s.d.=2.02), and non-alcoholic drinkers 2.73 (s.d.=0.78) with probability-p<0.001. This, even in the three cases, were traditional methods of evaluation, such as CAGE, SMAST questionnaires and SGOT, τGGT, SGPT liver tests of harmful alcohol consumption, were used have failed.

Ethanol was consumed in a solution made of 95% grain alcohol to 10 parts by volume of cold orange juice. This dose was divided into three equal parts. Each part of the prepared alcohol cocktail was slowly ingested over of five-minute periods (for a total of 15 minutes).

The BAC readings used in tables 1 and 2 were obtained using breath samples taken with the INTOXIMETER EC/IR 3000 made by Intoximeters, Inc. of St. Louis, Mo. This device has a rated accuracy of ±0.001 (1 mg/dl). The machine was reprogrammed to increase ethanol values by five percent from factory settings to more accurately reflect actual BAC. Deep lung breath samples are highly correlated with blood alcohol concentration measured by Gas Chromatography (GC). Our laboratory comparison of a breath by breathalyzer and blood alcohol concentration measured at the same time by GC showed a blood/breath ratio of 0.994 with a correlation of 0.99.

The Transdermal Alcohol Levels (TAL) were estimated by the Transdermal Alcohol Sensor/Recorder (TAS). These devices were made by Giner Inc. of Waltham, Mass. The TAS is a novel, experimental device consisting of an electrochemical sensor that detects ethanol, and a data acquisition-recording circuitry. During the test, the sensor was placed over the skin surface and continuously oxidizes excreted ethanol. The oxidation current provides a direct measurement of local ethanol vapor concentration.

Despite the similar peak in the BAC for non-alcoholic male 69.7 (s.d.=8.49) and female 68.2 (s.d.=8.98) tested individuals, the method is capable of detecting a gender difference in ABA. The value of Index-K for women is 3.59 (s.d.=1.07) compared to the Index-K for non-alcoholic men of 2.74 (s.d.=0.77). The probability of <0.001 suggests that a female's protective barrier against alcohol in general is weaker than the non-alcoholic male.

The method constitutes on a way to quantify ABA in humans which allows for separation between relatively "safe" and harmful alcohol consumption for any given individual. In the present recognition, based on the BAC data from 83 experimental subjects, the verge for "safe" alcohol consumption would be a particular value for the Index-K of 3.4 or less.

Although the Index-K and the method of using the same according to present invention has been described in foregoing specification with considerable detail, it is to be understood that modifications may be made to the invention which do not exceed the scope of the appended claims and modified forms of the present invention done by other skilled in the art to which the invention pertains will be considered infringements of this invention when those modified forms fall within the claimed scope of this invention.

Also, because the proposed method is universal and interest in quantificaiton of catabolism for substances other than ethanol in human body will increase in future studies, be advised that applying the Index-K concept in such research without the inventor's assent will be considered encroachment on the author's rights.

What I claim as my invention is:

1. A method for quantifying an individual's catabolic activity for alcohol, comprising the steps of:

a. providing a single dose of alcohol of standardized alcohol intake to an individual;

b. repeatedly measuring the subject's Breath (Blood) Alcohol Concentration before it reaches zero;

c. based on the measurements obtained in step b, plotting the alcohol concentration levels for an individual versus time and using computerized techniques to obtain value of the Area Under the Curve (AUC) for the ascending and descending parts of the plotted data;

d. dividing the individual's alcohol eliminition AUC as determined by the descending plotted part of the curve in step c by the plotted AUC for the ascending part of the pharmacokinetical curve to obtain a representation of alcohol catabolism presented as an Index-K value; and e. determining said Index-K according to the formula:

$$\text{Index} - K = \frac{AUC\text{elim}}{AUC\text{abs-distr}}$$

wherein AUCelim is defined as the elimination of ethanol and is equal to the descending segment of the plotted curve, and the term AUCabs-distr is defined as the sum of the absorption-distribution of ethanol and is equal to the area under the plotted ascending part of the pharmacokinctical curve.

2. The invention as claimed in claim 1, wherein said dose of standardized alcohol in step a is calculated by one of two commonly used method: based on the total body water volume required to achieve a 80 mg/dl blood alcohol concentration, or by 0.75 or 0.65 ml per one Kg of total body weight for male and female individuals, respectively.

* * * * *